(12) United States Patent
Yu

(10) Patent No.: US 6,305,617 B1
(45) Date of Patent: Oct. 23, 2001

(54) OSCILLATING DISK DENTAL HYGIENE DEVICE

(76) Inventor: Michael Yu, 1720 Shakespeare Dr., Concord, CA (US) 94521

( * ) Notice: Subject to any disclaimer, the term of this patent is extended or adjusted under 35 U.S.C. 154(b) by 0 days.

(21) Appl. No.: 09/495,884

(22) Filed: Feb. 1, 2000

Related U.S. Application Data

(63) Continuation-in-part of application No. 09/013,477, filed on Jan. 26, 1998, which is a continuation-in-part of application No. 08/517,915, filed on Aug. 22, 1995, now Pat. No. 5,711,482, which is a continuation-in-part of application No. 08/238,063, filed on May 3, 1994, now abandoned.

(51) Int. Cl.$^7$ ............... B05B 17/00; B05B 1/08; B05B 3/04
(52) U.S. Cl. ........................ 239/102.1; 239/381
(58) Field of Search .................. 239/1, 381, 101, 239/380, 382, 383, 389, 390, 391–395, 102.1, 102.2; 433/80, 88, 215, 216, 110; 601/165, 162

(56) References Cited

U.S. PATENT DOCUMENTS

| | | | |
|---|---|---|---|
| 2,554,790 | 5/1951 | Miller | 138/43 |
| 3,273,803 | 9/1966 | Crowley | 239/457 |
| 3,734,410 | * 5/1973 | Bruno | 239/102 |
| 3,777,980 | 12/1973 | Allport | 239/272 |
| 3,795,319 | * 3/1974 | Luthi et al. | 239/409 |
| 3,929,287 | * 12/1975 | Givler et al. | 239/102 |
| 4,018,385 | * 4/1977 | Bruno | 239/102 |
| 4,141,502 | * 2/1979 | Grohe | 239/381 |
| 4,151,957 | * 5/1979 | Gecewicz et al. | 239/381 |
| 4,369,923 | 1/1983 | Bron | 239/542 |
| 4,478,367 | * 10/1984 | Petursson | 239/381 |
| 4,718,608 | 1/1988 | Mehoudar | 239/542 |
| 5,065,648 | * 11/1991 | Hocfbaum, Jr. | 81/64 |
| 5,279,462 | 1/1994 | Mehoudar | 239/542 |
| 5,294,058 | 3/1994 | Einav | 239/533.1 |
| 5,295,506 | 3/1994 | Smith | 137/271 |
| 5,461,744 | * 10/1995 | Merbach | 15/22.1 |
| 5,711,482 | 1/1998 | Yu | 239/11 |

FOREIGN PATENT DOCUMENTS

| | | | |
|---|---|---|---|
| 2378444 | 8/1978 | (FR) . | |
| 2614557 | 11/1988 | (FR) | 239/542 |
| 2009573 | 6/1979 | (GB) . | |
| 1191027 | 11/1985 | (SU) | 239/542 |
| 1509002 | 9/1989 | (SU) | 239/542 |
| 8402828 | 8/1984 | (WO) | 239/542 |

* cited by examiner

Primary Examiner—David A. Scherbel
Assistant Examiner—Davis Hwu
(74) Attorney, Agent, or Firm—Munsch Hardt Kopf & Harr P.C.

(57) ABSTRACT

An oscillating disk dental hygiene device of the present invention includes a quick coupling assembly having a first stage adapted to be coupled to a water source fixture and a second stage adapted to be quickly attachable and detachable from the first stage; a main housing defining a water chamber and having an inlet and an outlet, the inlet being coupled with the second stage of the quick coupling assembly; and a disk defining at least one opening therein and being disposed in the water chamber, the disk adapted to oscillate between a first substantially neutral position and a second position substantially obstructing the outlet when water entering the water chamber via the inlet has a pressure within a predetermined range, the oscillating disk creating a pulsating water stream exiting the water chamber via the outlet. A hand held nozzle is coupled to the outlet and is adapted to concentrate and direct the pulsating water stream into a pulsating water jet.

41 Claims, 2 Drawing Sheets

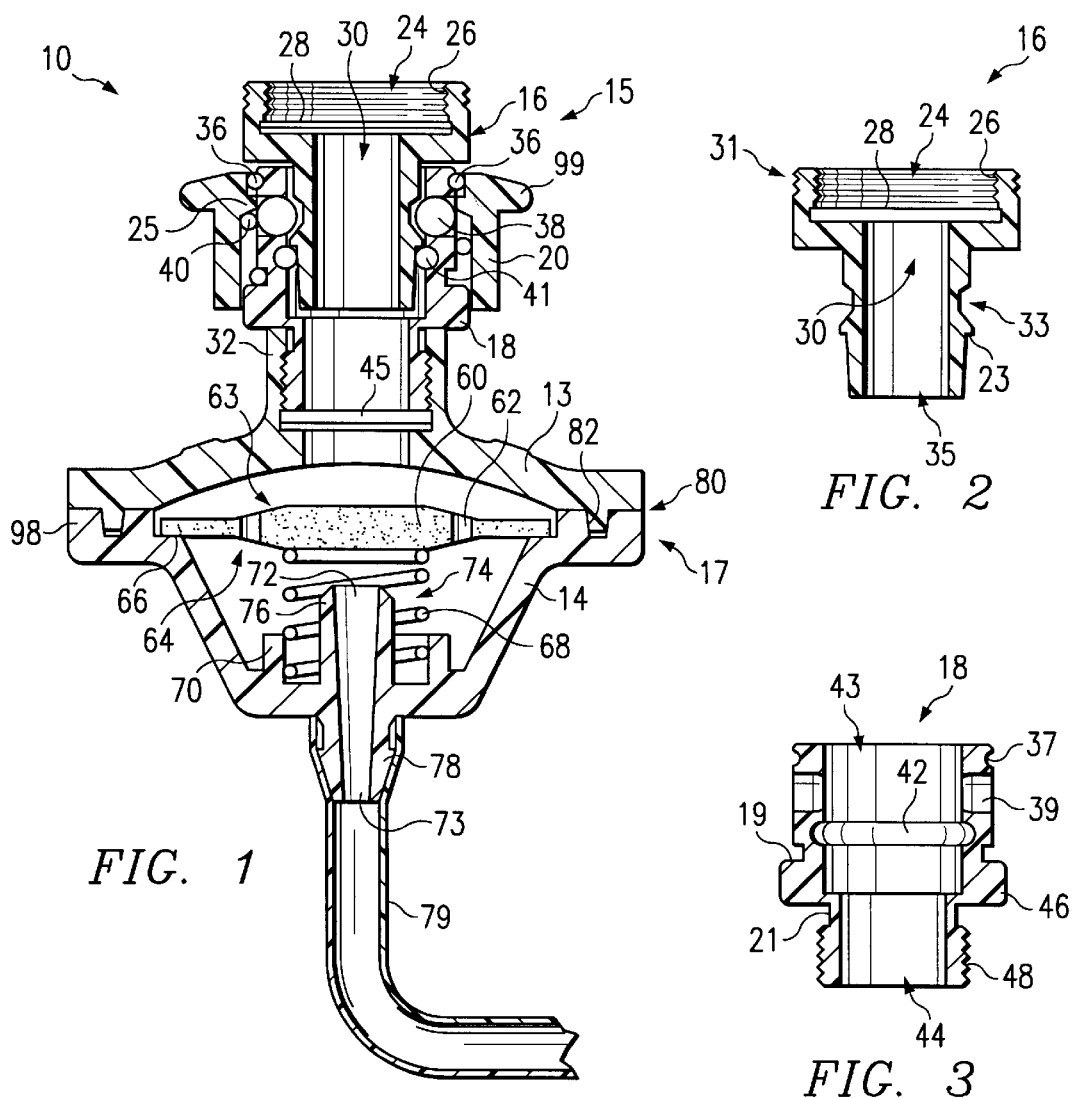
FIG. 1
FIG. 2
FIG. 3
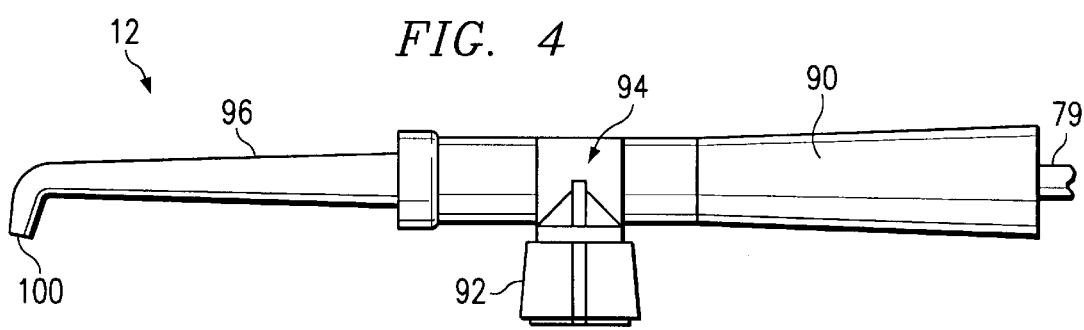
FIG. 4

OSCILLATING DISK DENTAL HYGIENE DEVICE

RELATED PATENT APPLICATION

This application is a continuation-in-part application of U.S. Ser. No. 09/013,477, entitled Oscillating Disk Devices, filed on Jan. 26, 1998, which is a continuation-in-part application of U.S. Ser. No. 08/517,915, filed Aug. 22, 1995, now U.S. Pat. No. 5,711,482, entitled Resilient Disk Drip Irrigation Devices, issued on Jan. 27, 1998 to Michael Yu, which are hereby incorporated herein by reference. U.S. Pat. No. 5,711,482 is a continuation-in-part application of U.S. application Ser. No. 08/238,063, filed May 3, 1994, and entitled "Resilient Disk Drip Irrigation Devices" by Michael Yu, now abandoned.

TECHNICAL FIELD OF THE INVENTION

This invention is related in general to the field of dental hygiene devices. More particularly, the invention is related to an oscillating disk dental hygiene device (WATERFLOS™).

BACKGROUND OF THE INVENTION

Many dental hygiene devices are on the market today. Some devices such as WATERPIK® generate a high-energy pulsating water jet for cleaning teeth. This method of cleaning is particularly useful when dental braces are installed. Pulsating water jets are also used for massaging the gums. These devices typically use a small reservoir of water as a water source. Complex mechanisms powered by electricity are used to create pulsating water waves and to expel them at high velocity.

The conventional devices have proven to be helpful in increasing and maintaining healthful teeth and gums and are recommended by dental professionals. However, these devices are inconvenient to use because the water reservoir must be refilled after each use and kept clean. The amount of water that can be used in each cleaning session without refill is also limited by the size of the reservoir. Furthermore, traditional devices are expensive, bulky and not portable for travel, and their complex mechanisms have many parts, which may wear and break down.

SUMMARY OF THE INVENTION

There is a need for dental hygiene devices that do not require complex mechanisms or the use of electricity. Furthermore, there is a need for a portable dental hygiene device that can be easily transported and is also easy to use. The proposed device is much smaller, easily portable and needs less cleaning after each use. It does not require electricity or contain complex working mechanisms, and most importantly it is less expensive to manufacture. This will be of benefit to all consumers, particularly lower income populations that need dental hygiene the most.

In one aspect of the invention, an oscillating disk dental hygiene device includes a quick coupling assembly having a first stage adapted to be coupled to a water source fixture such as bathroom faucet and a second stage adapted to be quickly attachable and detachable from the first stage; a main housing defining a water chamber and having an inlet and an outlet, the inlet being coupled with the second stage of the quick coupling assembly as a unit; and a disk defining at least one opening therein and being disposed in the water chamber. The disk is adapted to oscillate between a first substantially neutral position and a second position substantially obstructing the outlet discharge opening, when water entering the water chamber via the inlet has a pressure within a predetermined range, the oscillating disk creates a pulsating water stream exiting the water chamber via the outlet discharge. A hand-held nozzle is coupled to the outlet through flexible tubing and is adapted to concentrate and direct the pulsating water stream into a pulsating water jet nozzle.

In another aspect of the invention, a pulsating water wave generator includes a quick coupling assembly adapted to be coupled to a water source, and a main housing defining a water chamber and having an inlet and an outlet, the inlet being joined with the quick coupling assembly. A disk defining at least one opening therein is disposed in the water chamber; the disk has a reinforced center section and a surface area substantially greater than the outlet size. The disk is adapted to oscillate between a first substantially neutral position and a second position substantially obstructing the outlet discharge opening when water entering the water chamber via the inlet is within a predetermined pressure range. The oscillating disk creates a pulsating water stream exiting the water chamber via the outlet.

In yet another aspect of the invention, a method of generating a pulsating water jet to clean teeth and massage gums is provided. The method includes the steps of 1) Coupling an inlet of a pulsating water wave generator of an oscillating disk dental hygiene device onto a water source; 2) Providing water at a predetermined water pressure that enters the inlet and reaches the chamber of the pulsating water wave generator, then permits the water to flow through at least one opening defined in a free-floating disk positioned in the water chamber, the disk having an inlet side and an outlet side; 3) increasing the water pressure to a preset range at the inlet side of the disk due to a higher volume of pressurized water flowing into the inlet side than the amount of water able to discharge from the inlet side of the disk through the hole (or holes) in the disk to the outlet side (discharge side of the disk). This creates unbalanced pressure and pushes the disk against a biasing spring and toward a discharge opening protruding into the water chamber leading out to the outlet; 4) continuing to permit the water to flow through the at least one opening in the disk so connecting inlet and outlet sides of the disk and making it one body of water. As soon as the disk is close to closing the discharge opening, the discharge side is no longer at atmospheric pressure, to a point where water pressure on both sides of the disk should be equalized or almost equalized. The sudden surge of pressure at the discharge side wet surface, with the combined deflection rate of the compressed disk and the biasing spring causes the outlet side pressure to become greater than the inlet side. The pressure imbalance causes the disk to instantaneously return towards its neutral position spaced from the discharge opening. This action will be repeatedly instantly and will cause rapid oscillation. The rate of the oscillation is determined by the water discharge speed, distance of disk oscillation and the design of the device. In principle, if the discharge speed is two meters per second and the disk oscillation distance is 1 mm, the oscillation speed could be 1,000 cycles per second or less, depending on the configuration of the design.

BRIEF DESCRIPTION OF THE DRAWINGS

For a better understanding of the present invention, reference may be made to the accompanying drawings, in which:

FIG. 1 is a cross-sectional side view of the oscillating disk dental hygiene device WATERFLOS™ constructed according to an embodiment of the present invention;

FIG. 2 is a cross-sectional side view of a first stage of a quick coupling and filtering assembly of the oscillating disk dental hygiene device constructed according to an embodiment of the present invention;

FIG. 3 is a cross-sectional side view of a second stage of a quick coupling and filtering assembly of the oscillating disk dental hygiene device constructed according to an embodiment of the present invention;

FIG. 4 is a side view of a hand held nozzle constructed according to an embodiment of the present invention;

DETAILED DESCRIPTION OF THE INVENTION

Figure 5A:
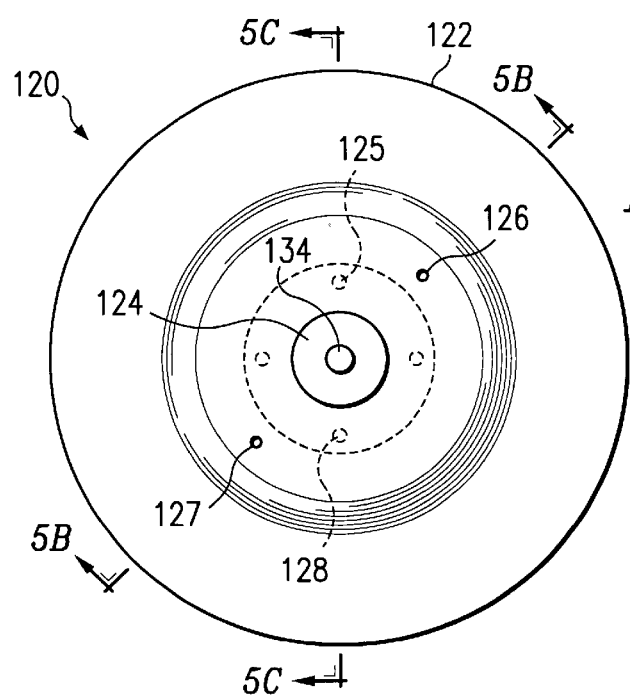
FIGS. 5A–5C are views of an embodiment of a combination disk.

The present invention, the oscillating disk dental hygiene device WATERFLOS™, is a further application of the innovative oscillating disk concept taught in U.S. Pat. No. 5,711,482, entitled Resilient Disk Drip Irrigation Devices issued to Michael Yu on Jan. 27, 1998. The previous invention uses the disk's deflection rate, as primary source to create oscillations and it is only able to handle light applications and is not able to handle most industrial applications. After years of experimentation it was found that even if using the best disk material the deflection rate will be exhausted or reduced after few million of cycles of oscillations, especially if using on high speed (with higher pressure) and high volume (discharge volume) operations, which are required in most industrial situations. A well-designed compression spring should be able to handle billions of cycles of oscillation. The present device is preferably designed to use a spring as a component to store energy instead of only using a resilient disk.

Another main concern is that of the material used for disk construction. Flexibility, resiliency, and resistance to aberrations are the main characteristics we are looking for, since these characteristics could provide better sealing and longevity in an industrial application. However, when pressure and discharge volumes increase, the disk could oscillate hundreds of cycles per second, pressure could reach hundreds psi, and a hard material (such as polycarbonate (PC) or a metal such as stainless steel) is needed to reinforce the center of the disk in the form of a support disk. The diameter of the hard support disk (inserted in the resilient disk) should be larger than the discharge opening.

During operation, the wet surface area at intake side is always under predetermined water pressure. But at discharge side of the disk is sandwiched by ever changing water pressure, except for the very center of the discharge side where the area facing the discharge opening is always at atmospheric pressure. This is a critical portion of the disk. If the disk is improperly designed and/or the configuration of the device is flawed, the disk can be easily damaged and will have little commercial value.

The discovery of using a spring and disk has widened the possible applications of this invention, for example, it can be used in pressure washers to make them much more effective, the high speed hammering action requires much less pressure to achieve the same effect, which results in energy savings. Pressurized water could also be used to operate a special jackhammer, by utilizing these principles, such a tool will use less energy and will not generate sparks, which is necessary in special applications. Oscillating disk technology can also be used to wash parts, equipment, household and commercial laundry and to emulsify or mix products. This technology can also be used to make industrial vibrators, etc. The principles of the present invention can also be used to send a 0/1 signal through water such as to communicate with submarines.

Hundreds of products can be based on this technology. The benefit of using this technology is its simplicity, its efficiency in converting potential energy to kinetic energy and its cost-effectiveness.

Referring to FIGS. 1–4, the oscillating disk dental device of the present invention includes a water propulsion system 10 adapted for attachment to a faucet or any water source (not shown) for receiving water flow therefrom, and a hand-held nozzle 12 coupled to pulsating water wave generator 10 for directing a pulsing water jet into the treatment areas.

Briefly, the main components of pulsating water wave generator 10 include a quick coupling and filtering assembly 15 coupled to a main housing 17 with a resilient disk 60 enclosed therein. Water flowing through quick coupling and filter assembly 15 and into main housing 17 at a predetermined flow rate or pressure causes resilient disk 60 to oscillate. The oscillatory motion of resilient disk 60 generates a strong pulsation in the water discharged from main housing 17. The pulsating water continues to hand-held tool 12 via a tubing 79 and finally exits a discharge tip 100 in hand-held nozzle 12 as a pulsating water jet. Tubing 79 may be constructed of any suitable plastic material that is flexible. The length of tubing 79 should be sufficient for a user to easily reach his/her mouth with hand held nozzle 12 without bending over at the waist. The pulsating water jet may be used to clean and floss teeth, dentures and other dental devices and to massage gums and other soft tissues.

It may be seen from studying FIGS. 1–3 that quick coupling and filtering assembly 15 includes a first stage 16 operable to be installed and attached to the water outlet of a faucet (not shown). First stage 16 includes an intake opening 24 which may be sized to fit conventional faucet outlets. Threading 31 or other suitable coupling means may be used to secure first stage 16 to the faucet. A screen filter 28 is disposed in first stage 16 across water passageway 30 thereof to filter out undesirable sand, debris and other foreign matter which may be present in the water. It may be seen that first stage 16 is adapted to replace the existing screen filter and/or aerator that is commonly installed on many faucets. First stage 16 further defines a water outlet 35 that leads into a second stage 18 of quick coupling and filtering assembly 15.

Second stage 18 is the lower portion of the quick coupling and filtering assembly 15 assembled with pulsating water wave generator 17 of the oscillating disk dental device as a assembly. This assembly can be quickly disengaged from the first stage upper portion of the quick coupling 16. The first stage 16 is the upper portion of the quick coupling which is screwed to a faucet to replace the original filter/ariater. Second stage 18 includes a water entry passageway 43 and a water exit passageway 44. Water outlet 35 of first stage 16 fits into water entry passageway 43 of second stage 18. A sealing ring or O-ring 41 is disposed at the interface between water outlet 35 and water entry passageway 43 to prevent water from backing up and leaking out of quick coupling and filtering assembly 15. A circumferential recess 42 formed in water entry passageway 43 of second stage 18 and a circumferential protruding rib 23 formed in the outer surface of water outlet 35 of first stage securely retains sealing ring 41.

First stage 16 and second stage 18 of quick coupling and filtering assembly 15 may be quickly engaged or disengaged by the actuation of a sliding lock mechanism 20. Sliding lock mechanism 20 may be biased by a helical coupling spring 40 disposed between sliding lock mechanism 20 and second stage 18. Coupling spring 40 may be seated in a crevice 19 against flange 46 of second stage 18. A retaining ring 36 is further disposed in a circumferential recess 37 formed in second stage against sliding lock mechanism 20 to maintain sliding lock mechanism 20 in the locked position. A ball bearing 38 is further disposed between second stage 18 and sliding lock mechanism 20 to keep second stage 18 engaged with first stage 16. A bearing seat 39 is created in second stage 18 to retain ball bearing 38. Note that a recess 33 is also formed in the exterior wall of water passageway 30 of first stage 16 to accommodate ball bearing 38. A circumferential locking flange 25 is formed on its inner surface. When sliding lock mechanism 20 is moved to its unlocked position toward main housing 17 (and away from the faucet), first stage 16 is released from second stage 18, thus disengaging pulsating water wave generator 10 from the faucet. It may be seen that when sliding lock mechanism 20 is in its locked position, locking flange 25 is maintained on one side of ball bearing 38 by coupling spring 40; when sliding lock mechanism 20 is in its unlocked position, locking flange 25 is manually forced past ball bearing 38 against coupling spring 40 to the other side of ball bearing 38. When the user releases the sliding lock mechanism, coupling spring 40 biases sliding lock mechanism 20 and locking flange 25 back to the locked position.

Lower Quick coupling half and filtering assembly includes threading on the outer surface of the wall defining water exit passageway 44 of second stage 18. Threading 48 is used to screw lower quick coupling half—to an inlet 32 of main housing 17 of pulsating water wave generator 10. This assembly is done at factory A filter 45 is disposed in inlet 32 leading to the water chamber of main housing 17. Filter 45 may be used as a secondary filter—to further remove smaller particulates from the water. Main housing 17 includes an upper housing portion 13 and a lower housing portion 14 coupled together to form the water chamber. The water chamber is divided by a resilient disk 60 into an inlet side 63 and an outlet side 64. Inlet side 63 faces inlet 32 and outlet side 64 faces discharge outlet 74. Disk 60 is positioned generally perpendicularly to the path of water entering inlet 32 and exiting discharge outlet 74. Upper housing portion 13 and lower housing portion 14 of main housing 17 may be coupled together a number of different ways. For example, appropriate threaded fitting, press-fitting, adhesives, bonding agents, quick coupling, or ultrasonic welding may be employed to form a water tight seal between the two housing portions. Preferably, at an interface 80 between upper and lower housing portions 13 and 14, mating ridges and notches 82 may be formed and sealed together by ultrasonic welding. Upper and lower housing portions 13 and 14 may be constructed from ABS, high density polypropylene, high density polyethylene, and other materials or combinations of materials.

Disk 60 is preferably constructed from high tensile strength materials that are resistant to abrasion. For example, some polyurethane composite materials may be used. Other materials such as natural latex, EPDM, VITON, silicone, metal or metal composites may also be used. Disk 60 includes one or more openings 62 which allows water on inlet side 63 of the water chamber to pass through to outlet side 64. More than one opening located diametrically are advantageous for evenly distributing the water pressure over the disk surface. The combined opening size of one or more openings 62 is preferably less than the size of the water passageway of inlet 32 and also less than the size of the water passageway of discharge outlet 74. Disk 60 may also be shaped with a thicker center section than its outer perimeters. The thicker center section helps to reinforce the areas of disk 60 that may encounter the most wear and pressure differential due to its oscillatory motion during operation. Other means of reinforcement may also be used as long as the oscillatory motion of the disk is not hindered. For example, a stronger material may be used in the center section of disk 60 than at the outer edges.

Figures 5B, 5C:
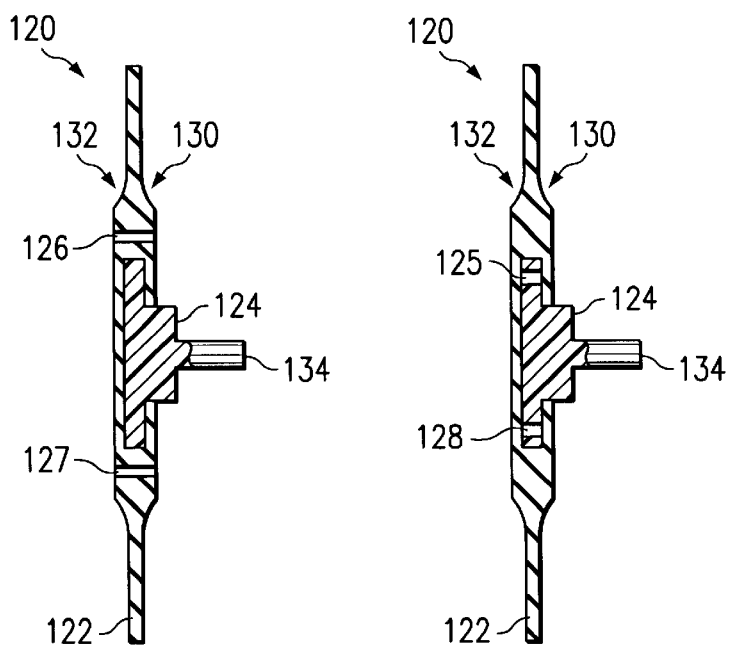

The construction of a combination disk 120 is shown in FIGS. 5A, 5B and 5C. Combination disk 120 includes a more rigid center portion 124 embedded in a disk 122 formed from an elastic and resilient material for extra reinforcement. Center portion 124 may include a circular center part that protrudes beyond the elastic material 122 of combination disk 120. Center disk portion 124 defines a plurality of openings that allow the elastic outer disk material to flow through and more securely bond with center disk portion. This allows the two materials to become a more integrally constructed disk. A center knob 134 is used for the purpose of providing a grip or handle that may be used to securely hold disk 120 while it is being manufactured. Center know 134 may be removed in a final steip of manufacture when disk 120 is installed in the dental device. Two diametrically opposed openings 126 and 127 in disk 120 are shown. Disk 120 further includes a tapering 130 and 132 in its outer edge to a thinner perimeter 122. The discharge surface of disk 120 is preferably covered with the elastic material. This improved disk is able to oscillate hundreds of cycles per second for long periods of time. Fittings may be used to fasten the hard center disk and the resilient disk together, but this often caused fitting fatigue as well as causing the hard disk to cut int the resilient disk during operation. The present invention preferably uses a hard disk encased or embedded within the resilient disk as a unit, and no fasteners are needed.

Disk 60 or 120 is supported so that it does not block a discharge opening 72 of discharge outlet 74 formed in lower housing portion 14. Disk 60 is supported at its outer perimeters by a shelf 66 formed in lower housing portion 14. Alternatively, the outer perimeter of disk 60 may be affixed to shelf 66 by bonding or other means. Disk 60 may also be supported in its center section by a helical compression spring 68. Compression spring 68 may be seated in a spring retaining wall 70 which holds compression spring 68 perpendicularly with respect to disk 60. Compression spring 68 is operable to store the energy forced upon it by the water pressure asserted against disk 60 at inlet side 63, and instantly releasing the stored energy to bounce disk 60 back toward inlet 32, thus generating the oscillatory motion. The operation of the oscillating disk dental device of the present invention is described in more detail below.

Discharge outlet 74 of lower housing portion 14 further includes a circular support column 76 surrounding discharge opening 72 that protrudes into outlet side 64 of the water chamber. It is preferable that the opening size of discharge opening 72 is larger than the opening size of a discharge tip 73 to increase the velocity of the exiting water stream. For example, discharge opening 72 may be twice as large as discharge tip opening 73. Discharge tip 73 is adapted to be inserted or otherwise connected with a length of tubing 79 leading to hand held nozzle 12. Discharge tip 73 may include an anchoring barb 78 that aids in retaining tubing 79. Anchoring barb 78 may include individual ridges or circumscribe discharge tip 73.

Hand held nozzle 12 includes an handle 90 which is coupled to tubing 79 and is the first to receive the pulsating water stream. A valve mechanism 94 with a control dial or knob 92 is contained in handle 90 to regulate the amount and thus the strength of water passing through a nozzle 96 and exiting its tip 100. Valve mechanism 94 may be operable to adjust the water passageway from fully closed to wide open, for example. Nozzle tip 100 may be manipulated by the user to precisely direct the pulsating water jet to targeted spots within the oral cavity.

Figure 6:
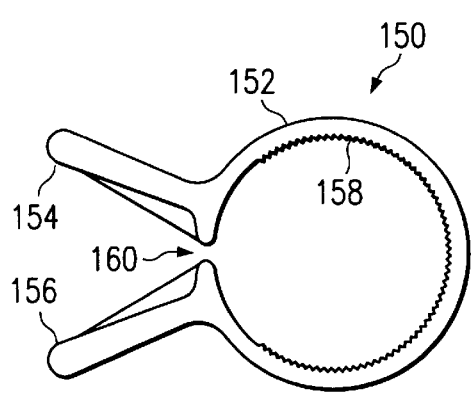
FIG. 6 is a perspective view of a clamping tool which may be used to facilitate the installation of the oscillating dental hygiene device of the present invention.

FIG. 6 is a top view of a faucet change out tool 150 constructed according to the teaching of the present invention. Tool 150 may be used to aid in the installation of oscillating disk dental device 10 onto a water source such as a faucet. Tool 150 includes a ring 152 with an opening 160 which terminates in two levers 154 and 156 that may be pinched together to tighten ring 152 around a faucet fitting. Teeth 158 formed along the inside circumference of ring 152 enable a more secure grip. Tool 150 may be used to remove the pre-existing aerating filter from the faucet and to install first stage 16 of dental device 10 onto the faucet.

In operation, second stage 18 may be quickly attached to first stage 16 by first moving sliding lock mechanism 20 from its locked position to its unlocked position and then positioning the opening of second stage water entry passageway 43 over water outlet 35 of first stage 16. In this manner, outlet 35 of first stage 16 is inserted into inlet 43 of second stage 18. When the user releases sliding lock mechanism 20, second stage 18 becomes securely attached to first stage 16, and thus attaching the oscillating disk dental device to the faucet or some water source of at least several psi. The user may conveniently brace his/her index and middle fingers against main housing outer rim 98 and his/her thumb against a collar 99 of sliding lock mechanism 20 and squeezing the fingers and thumbs toward one another to cause sliding lock mechanism 20 to force against coupling spring 40 and slide back to its unlocked position. When the fingers or thumbs are released or relaxed, sliding lock mechanism 20 is forced back to its locked position by coupling spring 40.

After the user has quickly attached the dental device to the water source or faucet, water flow may be started. The term water herein is loosely used to refer to any liquid, which may contain dental treatment solutions such as fluoride, chlorhexidine gluconate, etc. As water enters intake 24 of first stage 16, it is filtered by screen filters 28 and 45. The water then enters inlet side 63 of the water chamber and begin to exert pressure on disk 60. The initial water pressure pushes disk 60 against supporting shelf 66 at its outer edges and against compression spring 68 at its center. Water flows freely through the one or more openings 62 in the disk 60 and exits the main housing through the discharge outlet 74.

As water pressure increases to 20 or 40 psi for example, the pressurized water pushes against inlet side 63 of disk 60, and continues to push it firmly against shelf 66. Because the disk opening 62 size is much smaller than the water intake 30 diameter, this causes the water pressure to steadily increases at the inlet side 63 of disk 60. When the water pressure at inlet side 63 of disk 60 reaches a higher pressure than the deflection rate of resilient disk 60 and compression spring 68, disk 60 starts to advance toward discharge outlet 74. Prior to resilient disk 60 being pushed against support column 76 and the discharge outlet opening, the outlet side of resilient disk 60 is at or near atmospheric pressure because it is open to the atmosphere through discharge outlet 74. Water continues to pass through one or more openings 62 in disk 60 and joins the body of water on outlet side of disk 60 until the water pressure at outlet side 64 of resilient disk 60 is equalized or close to equalized with the intake side water pressure, combined with the compression energy stored in compression spring 68 and the deflection rate of disk 60 equals and then exceeds the water pressure at inlet side 63 of disk 60. At the instant the outlet side pressure equalizes and exceeds the inlet side pressure, compressed spring 68 and resilient disk 60 bounce back toward their original central position to unload their tension. Suddenly outlet side 64 of resilient disk 60 is open to the atmosphere, and the outlet side water pressure is instantly reduced to atmospheric pressure again. Disk 60 is therefore once again being pushed toward and eventually blocking discharge outlet 74 which increases the pressure on the outlet side. This action is repeated to create an oscillatory motion or plunging effect in the disk. The oscillatory motion of the disk creates a pulsating wave or motion in the water exiting from main housing 17 through discharge outlet 74. The narrowing of the water passageway in discharge outlet 74 as the water exits discharge tip 73 further increases the pulsating water stream velocity. The pulsating water stream travels through tubing 79 and enters hand held nozzle 12. The user may adjust the water pressure of the pulsating water jet exiting nozzle tip 100 by turning control dial 92 in one direction or the other.

The dental hygiene device of the present invention is preferably adapted to operate in this manner with a wide range of water pressures common to typical residential plumbing systems. For example, water pressures between 25 and 80 psi satisfactorily cause the dental device disk to oscillate approximately in the range of 25 to 100 cycles per second. When the water pressure is under or exceeds this range, disk 60 may not oscillate. The duration, the frequency, and all other performance parameters of the oscillation operation of the disk can be controlled by preset conditions. The major control parameters include the deflection rate of resilient disk 60, water pressure, total disk opening size, the ratio of disk opening size to the intake passageway 30, and the distance between shelf 66 and supporting column 76. Further, the proportion of the wet surface area on the outlet side of the disk (defined as the surface area of the disk minus the disk surface area covered by the shelf) to the discharge outlet opening size. The ratio is preferably greater than 10:1.

The speed and performance of oscillation depend on the design of the device and water pressure, but the major factors of the design are:

At set pressure of the water supply, the ratio of the intake volume to the volume of the water able to pass through the hole (or holes) in the disk to the discharge side is important. The volume of the water supply from the intake should be many times greater than the volume of water passing through the disk. If the difference between these volumes is not great enough it will cause the disk to slow down or stop oscillating. Within certain parameters, if the difference in volume increases, the oscillating speed generally increases and the displacement of the disk in oscillation decreases.

The minimum amount of water able to pass through the hole (or holes) in the disk must be taken into consideration in the design of the disk. When the disk bounces back to its neutral position it will create a void at the outlet side, this void must be replaced by water passing through the hole(s) in the disk at the same rate. If not, it will create a vacuum at the discharge side when the disk moves away from the discharge opening towards the neutral position. This will reduce efficiency and may cause the oscillation to stop.

At the intake side, to calculate the total surface area of the disk, deduct the surface area of the supporting shelf and the hole (or holes) in the disk. This surface area is referred to as the wet surface of the disk. The intake side is constantly under pressure during operation.

At the discharge side of the disk, the wet surface area is same size as the intake side minus the discharge opening size because the disk is pressed into the discharge opening which is at atmospheric pressure. During operation, water pressure at the discharge side changes rapidly, depending on whether the discharge opening is open or closed to the atmosphere.

In theory, if the discharge opening is completely in the open position, the water pressure at the discharge side should be at or close to atmospheric pressure, the spring and the disk should also be in a more relaxed state. At this moment there is none or little pressure at the discharge side of the disk. Water pressure at the intake side has not changed and it will push the disk against the spring towards the discharge opening. The increasingly compressed spring and disk will cause the deflection rate to increase, and the shrinking opening size also will increase the water pressure at the discharge side. When the discharge opening is completely closed, the force (pressure) at the discharge side will reach a maximum. The stored energy includes the sudden surge of water pressure at the discharge side of the disk wet surface, and the maximum deflection rate of the spring and disk. These combined forces are greater than the intake side total wet surface water pressure. This force will push the disk back towards to the neutral position away from the discharge opening. In this process all the energy stored in the spring and disk will be exhausted and water pressure at the discharge side will return towards to atmospheric pressure. This action will be repeated again and again, causing rapid oscillation. At higher pressures, with certain designs the oscillation could reach hundreds cycles per second.

In practice, during operation, the disk generally will not bounce all the way back to a completely neutral position, and the discharge opening is not necessarily 100% closed.

For practical purposes, the design of the device is designed in such a way as to make the disk return to a neutral position before the discharge opening completely closes. This will prevent the disk from making hard contact with discharge opening and will prolong the life of the disk and discharge opening.

The instant loss of pressure at the outlet side permits the disk to be pushed once again against the biasing spring toward the discharge opening by the intake water pressure, causing a continuous oscillating motion in the disk that generates pulsating water waves. The oscillation parameters of the current device (WATERFLOS™) is set at 30 to 80 psi, outside these parameters the oscillation will stop, but the water will continue to flow through this device. This is another advantage of this device; it allows the user to adjust the flow of water to stop the oscillation. However, changing the settings can alter the oscillation range. The speed of oscillation depends on the design of the device and the water pressure, both which can be controlled by the operator. The operator can use a knob on the hand-piece to regulate and control the volume and speed. At 50 psi oscillations can reach 40 to 70 cycles per second (this depends on the set up of the device). The final step is ejecting and directing the pulsating water waves in the form of a pulsating water jet.

When the user finishes his/her oral hygiene routine with the oscillatory disk dental device, it may be quickly decoupled from first stage 16 so that the faucet may be operable for its normal usage.

Unlike conventional devices, the dental hygiene device of the present invention is a simple mechanical device that does not use electricity, that does not have a limited water source, and is easily portable for travel.

A larger scale of the pulsating water wave generator may be used in industrial applications such as industrial cleaning, homogenization, mixing and emulsifying. In such applications, a rigid metallic disk with some form of reinforcement is recommended. The disk may be reinforced with a plate bolted thereto, for example.

Although several embodiments of the present invention and its advantages have been described in detail, it should be understood that mutations, changes, substitutions, transformations, modifications, variations, and alterations can be made therein without departing from the teachings of the present invention, the spirit and scope of the invention being set forth by the appended claims.

What is claimed is:

1. An oscillating disk dental hygiene device, comprising:
   a quick coupling assembly having a first stage adapted to be coupled to a water source fixture and a second stage adapted to be quickly attachable and detachable from the first stage;
   a main housing defining a water chamber and having an inlet and an outlet, the inlet being coupled with the second stage of the quick coupling assembly;
   a disk defining at least one opening therein and being disposed in the water chamber, the disk adapted to oscillate between a first substantially neutral position and a second position substantially obstructing the outlet discharge opening, when water entering the water chamber via the inlet has a pressure within a predetermined range, the oscillating disk creating a pulsating water stream exiting the water chamber via the outlet; and
   a hand held nozzle coupled to the outlet with flexible tube as conduit and adapted to concentrate and direct the pulsating water stream into a pulsating water jet.

2. The oscillating disk dental hygiene device, as set forth in claim 1, wherein the disk is generally circular with a center section thicker than its outer perimeter.

3. The oscillating disk dental hygiene device, as set forth in claim 1, wherein the disk includes a rigid reinforcing center portion.

4. The oscillating disk dental hygiene device, as set forth in claim 1, further comprising a biasing assembly substantially supporting the disk and maintaining a distance between the disk and the outlet when the disk is in the first substantially neutral position.

5. The oscillating disk dental hygiene device, as set forth in claim 4, wherein the biasing assembly generally supports a center section of the disk.

6. The oscillating disk dental hygiene device, as set forth in claim 1, wherein the main housing further comprises a shelf supporting the disk and maintaining a distance between the disk and the outlet when the disk is in the first position.

7. The oscillating disk dental hygiene device, as set forth in claim 6, wherein the shelf generally supports an outer perimeter of the disk.

8. The oscillating disk dental hygiene device, as set forth in claim 1, wherein the outlet is defined within a supporting column protruding into the water chamber.

9. The oscillating disk dental hygiene device, as set forth in claim 1, further comprising at least one filter disposed in the inlet operable to trap particulates in the water prior to entering into the water chamber.

10. The oscillating disk dental hygiene device, as set forth in claim 1, wherein the disk defines at least one opening.

11. The oscillating disk dental hygiene device, as set forth in claim 1, wherein the water entering in the inlet is greater than the water passing through the disk opening.

12. The oscillating disk dental hygiene device, as set forth in claim 1, wherein the inlet size is larger than the outlet size.

13. The oscillating disk dental hygiene device, as set forth in claim 1, wherein a wet surface area of the disk minus the outlet opening size is substantially greater than the outlet opening size.

14. The oscillating disk dental hygiene device, as set forth in claim 1, wherein the disk defines at least one opening therein.

15. The oscillating disk dental hygiene device, as set forth in claim 1, wherein the quick coupling assembly further comprises a seal disposed between the first and second stages to prevent water leakage from therebetween.

16. The oscillating disk dental hygiene device, as set forth in claim 1, wherein the quick coupling assembly further comprises a sliding lock mechanism operable to quickly attach the second stage to the first stage and to quickly detach the second stage from the first stage.

17. The oscillating disk dental hygiene device, as set forth in claim 16, wherein the sliding lock mechanism further comprises:
   a coupling spring operable to bias the sliding lock mechanism to a locked position from an unlocked position;
   a ball bearing disposed between the first stage and the second stage; and
   a locking flange engageable with the ball bearing to lock and unlock the second stage with the first stage.

18. The oscillating disk dental hygiene device, as set forth in claim 16, wherein the main housing comprises:
   an upper housing portion defining the inlet;
   a lower housing portion coupled to the upper housing portion and defining the outlet, the upper and lower housing portions defining the water chamber therebetween.

19. The oscillating disk dental hygiene device, as set forth in claim 1, further comprising:
   a length of tubing coupling the hand held nozzle to the main housing;
   a connecting barb in fluid conductivity with the water chamber and coupled to the tubing, the connecting barb having an anchoring barb providing increased friction between the connecting barb and the tubing.

20. The oscillating disk dental hygiene device, as set forth in claim 1, wherein the hand held nozzle comprises:
   a valve assembly operable to adjust the amount of water flow through the hand held nozzle; and
   a control knob operable to open and close the valve assembly to control water flow.

21. The oscillating disk dental hygiene device, as set forth in claim 1, wherein the disk comprises:
   a rigid center disk embedded in an elastic outer disk.

22. A pulsating water wave generator, comprising:
   a quick coupling assembly adapted to be coupled to a water source;
   a main housing defining a water chamber and having an inlet and an outlet, the inlet being joined with the quick coupling assembly;
   a disk defining at least one opening therein and being disposed in the water chamber, the disk having a reinforced center section and having a surface area substantially greater than the outlet size, the disk being adapted to oscillate between a first substantially open position away from the discharge outlet, and a second position substantially obstructing the outlet when water entering the water chamber via the inlet is within a predetermined pressure range, the oscillating disk creating a pulsating water stream exiting the water chamber via the outlet.

23. The pulsating water wave generator, as set forth in claim 22, wherein the disk is generally circular with a center section thicker than its outer perimeter.

24. The pulsating water wave generator, as set forth in claim 23, wherein the disk comprises a center disk constructed of a hard material coupled to an elastic disk facing the outlet.

25. The pulsating water wave generator, as set forth in claim 22, further comprising a biasing assembly substantially supporting the disk and maintaining a distance between the disk and the discharge outlet when the disk is in the first position.

26. The pulsating water wave generator, as set forth in claim 25 wherein the biasing assembly generally supports a center section of the disk.

27. The pulsating water wave generator, as set forth in claim 22, wherein the main housing further comprises a shelf supporting the disk and maintaining a distance between the disk and the outlet when the disk is in the first position.

28. The pulsating water wave generator, as set forth in claim 27, wherein the shelf generally supports an outer perimeter of the disk, and a spring generally supports center of the disk.

29. The pulsating water wave generator, as set forth in claim 22, wherein the outlet is defined within a supporting column protruding into the water chamber.

30. The pulsating water wave generator, as set forth in claim 22, further comprising at least one filter disposed in the inlet operable to trap particulates in the water prior to entering into the water chamber.

31. The pulsating water wave generator, as set forth in claim 22, wherein the disk defines at least one opening or two and more diametrically opposed openings.

32. The pulsating water wave generator, as set forth in claim 22, wherein a wet surface area at discharge side of the disk minus the outlet opening size is substantially greater than the outlet opening size.

33. The pulsating water wave generator, as set forth in claim 22, wherein the quick coupling assembly further comprises:
   a first stage adapted to be coupled to the water source fixture;
   a second stage adapted to be quickly attachable and detachable from the first stage;
   a seal disposed between the first and second stages to prevent water leakage from therebetween.

34. The pulsating water wave generator, as set forth in claim 22, wherein the quick coupling assembly further comprises a sliding lock mechanism operable to quickly attach the second stage to the first stage and to quickly detach the second stage from the first stage.

35. The pulsating water wave generator, as set forth in claim 34, wherein the sliding lock mechanism further comprises:
   a coupling spring operable to bias the sliding lock mechanism to a locked position from an unlocked position;
   a ball bearing disposed between the first stage and the second stage; and
   a locking flange engageable with the ball bearing to lock and unlock the second stage with the first stage.

36. The pulsating water wave generator, as set forth in claim 34, wherein the main housing comprises:

an upper housing portion defining the inlet;

a lower housing portion coupled to the upper housing portion and defining the outlet, the upper and lower housing portions defining the water chamber there between.

37. The pulsating water wave generator, as set forth in claim 22, further comprising:

a hand held nozzle;

a length of tubing coupling the hand held nozzle to the main housing; and a discharge tip in fluid conductivity with the water chamber and coupled to the tubing, the connecting tip having an anchoring barb providing increased friction between the connecting tip and the tubing.

38. The pulsating water wave generator, as set forth in claim 37, wherein the hand held nozzle comprises:

a valve assembly operable to adjust the amount of water flow through the hand held nozzle; and a control knob operable to open and close the valve assembly to control water flow.

39. The pulsating water wave generator, as set forth in claim 22, being used for industrial cleaning applications.

40. The pulsating water wave generator, as set forth in claim 22, being used for industrial mixing/emulsifying applications.

41. A method of generating pulsating water jet to clean teeth and massage gums, and comprising:

coupling an inlet of a pulsating water wave generator of an oscillating disk dental hygiene device onto a water source;

providing water at a predetermined water pressure entering the inlet and reaching a water chamber of the pulsating water wave generator, and permitting the water to flow through at least one opening defined in a free-floating disk positioned in the water chamber, the disk having an inlet side and an outlet side;

increasing the water pressure at the inlet side of the disk due to the inlet being greater than at least one opening of the disk, the water pressure being built up at the inlet side of the disk rapidly, outlet side water being discharged and not able to build much pressure, the pressure unbalance between the inlet and outlet side pushing the disk against a biasing spring and toward the outlet opening protruding into the water chamber leading out to the outlet;

continuing to permit the water to flow through the at least one opening in the disk so that when the outlet side water pressure equalizes or nearly equalizes with the inlet pressure combined with the defection rate of the compressed disk and the biasing spring, causing greater pressure at the outlet side of the disk than the inlet side, the disk instantaneously returns toward to its neutral position spaced from the discharge opening;

again permitting the disk to be pushed against the biasing spring toward the discharge opening by the intake water pressure, causing a continuous oscillating motion in the disk thereby creating pulsating water waves; and ejecting and directing the pulsating water waves in the form of a pulsating water jet.

* * * * *